United States Patent [19]
Hunziker

[11] Patent Number: 5,910,111
[45] Date of Patent: Jun. 8, 1999

[54] DISPLAY OF HEART MOTION

[76] Inventor: Patrick Hunziker, 79 Curtis St., Somerville, Mass. 02144

[21] Appl. No.: 08/941,150

[22] Filed: Sep. 30, 1997

[51] Int. Cl.$^6$ .................................................... A61B 5/05
[52] U.S. Cl. ............................................. 600/407; 359/23
[58] Field of Search .................................... 600/407, 437; 359/1, 22, 32, 33, 901; 73/603; 348/40; 250/550; 356/347; 430/1

[56] References Cited

U.S. PATENT DOCUMENTS

| | | | |
|---|---|---|---|
| 3,889,226 | 6/1975 | Hildebrand | 340/5 H |
| 3,937,066 | 2/1976 | Green et al. | 73/67.5 |
| 3,937,555 | 2/1976 | Benton . | |
| 4,159,462 | 6/1979 | Rocha et al. | 73/626 |
| 4,337,992 | 7/1982 | Johnson . | |
| 4,415,225 | 11/1983 | Benton et al. . | |
| 4,498,729 | 2/1985 | Benton . | |
| 4,834,476 | 5/1989 | Benton . | |
| 5,038,791 | 8/1991 | Collins et al. . | |
| 5,098,176 | 3/1992 | Wolf | 359/11 |
| 5,191,449 | 3/1993 | Newswanger . | |
| 5,245,448 | 9/1993 | Waits . | |
| 5,503,152 | 4/1996 | Oakley et al. | 600/437 |
| 5,519,517 | 5/1996 | Redfield et al. . | |
| 5,526,327 | 6/1996 | Cordova, Jr. . | |
| 5,543,251 | 8/1996 | Taylor | 430/1 |
| 5,548,419 | 8/1996 | Adrian et al. . | |
| 5,553,618 | 9/1996 | Suzuki et al. | 600/407 |
| 5,592,313 | 1/1997 | Hart . | |
| 5,722,411 | 3/1998 | Suzuki et al. | 600/439 |

OTHER PUBLICATIONS

Klug M.A. A compact prototype one–step ultragram printer. SPIE Proceeding #1914, 'Practical Holography VII', pp. 15–19 (1993).

Vannan M.A. et al. Volumetric multiplexed transmission holography of the heart with echocardiographic data. J Am Soc Echocardiography 1995; 8: 567–575.

Graham Saxby. Holography in Biology and Medicine. In: Graham Saxby, Practical Holography, 2nd edition, 1994, pp. 429–435 Prentice–Hall, London.

*Primary Examiner*—Brian Casler

[57] ABSTRACT

According to the invention, a method to process heart motion image data into a portable display medium is provided. An image sequence of heart motion is provided. Image sequences are incorporated in angularly multiplexed holograms so that the parallax, i.e. the relative position of observer and holographic medium, encodes heart motion. This way, a change in the viewing angle of the printed hologram leads to the perception of the complete heart cycle. Using this technique, it is possible to incorporate a complete temporal image sequence of the beating human heart to a single printable image which can be used for display, storage, documentation and reporting.

9 Claims, 2 Drawing Sheets

2.1

2.2

2.3

DISPLAY OF HEART MOTION

FIELD OF THE INVENTION

The present invention relates to a method of displaying heart motion, acquired by medical imaging techniques.

BACKGROUND OF THE INVENTION

Since prehistoric times, man has been able to capture and depict objects only in the form of static two-dimensional images. Only a century ago did it become possible to capture the motion of an object in the form of a series of single frames and to play them back as an animation. In echocardiography, motion was first represented in M-mode images, in which one axis of the display showed the echoes of a single scanline while a second axis coded time. The advent of two-dimensional echocardiographic imaging led to the current method of representing real time myocardial motion as video sequences. This development improved the understanding of cardiac structure in vivo and added new insights into cardiac function. However, viewing cardiac motion in a compact display becomes more cumbersome with 2D- compared to M-mode echocardiography.

Currently, echocardiograms are stored primarily on videotapes, but digital storage media are being used more frequently for echocardiograms as well as for magnetic resonance and other medical imaging techniques. However, the search and review of studies on videotapes is time consuming and impractical, and both video and digital storage media require expensive and heavy equipment. Simple printing of single echocardiographic frames (similar to what is routinely done in radiology) is not practical because motion, a principal information content of heart imaging, is lost if a frame is printed. No methods exist to display, in a printable format, a moving heart in two-dimensional or three-dimensional images. At the current time, echocardiography machine manufacturers are developing hardware and software that allow both the digital image acquisition and the presentation of echocardiographic studies on portable computers. Holography has been used to display static 3-dimensional images of the pelvis, the spine and the brain, by using computer tomography, magnetic resonance imaging and sonographic techniques to acquire image information. One description of holographic imaging of the heart was likewise limited to the representation of static images of a explanted animal heart.

In contrast to the above described applications in biomedicine, dynamic datasets containing object motion, mainly of the heart, as acquired by ultrasound, computer tomography or magnetic resonance tomography, contain a significantly higher amount of data, posing additional problems for representation in an understandable manner; application of holography to dynamic datasets of the beating heart has not been reported.

SUMMARY OF THE INVENTION

It is an object of the invention to display heart motion.

It is another object of the invention to display heart motion on a portable medium.

It is another object of the invention to process datasets acquired by medical imaging techniques, e.g. echocardiography, computer tomography and magnetic resonance imaging techniques, into a display format.

It is another object of the invention to process heart motion datasets into a format suitable for storage and reporting.

It is another object of the invention to provide a display technique enabling a review of multiple heart motion loops at the same time.

It is another object of the invention to provide a motion display in which motion can be slowed, stopped or reversed easily.

According to the invention, a method to process heart motion image data into a portable display medium is provided. Image datasets of heart motion are acquired by medical imaging techniques. The image datasets are exported from the acquisition machine in digital or analog format. After reformatting and postprocessing, the datasets are incorporated into angularly multiplexed holograms so that one parallax (i.e. the relative position of observer and holographic medium) encodes heart motion, thereby permitting the observer to perceive the motion of the complete heart cycle by tilting the hologram or changing his viewing position.

Image sequences can be, e.g., two- or three- dimensional image loops acquired by echocardiography, computer tomography, magnetic resonance imaging or other feasible imaging techniques. The vertical or the lateral parallax of a hologram is used to encode time; the other parallax encodes the three-dimensionality of the heart if desired. Any holographic production technique is applicable, provided it allows the introduction of temporally coded image sequences into the parallax of the resulting hologram.

The above and other objects, features and advantages of the present invention will be better understood from the following specification when read in conjunction with the accompanying drawings.

BRIEF DESCRIPTION OF THE DRAWINGS

Drawing 1

Process of representation of heart motion by temporally coded, angularly multiplexed holography:

Figure 1:
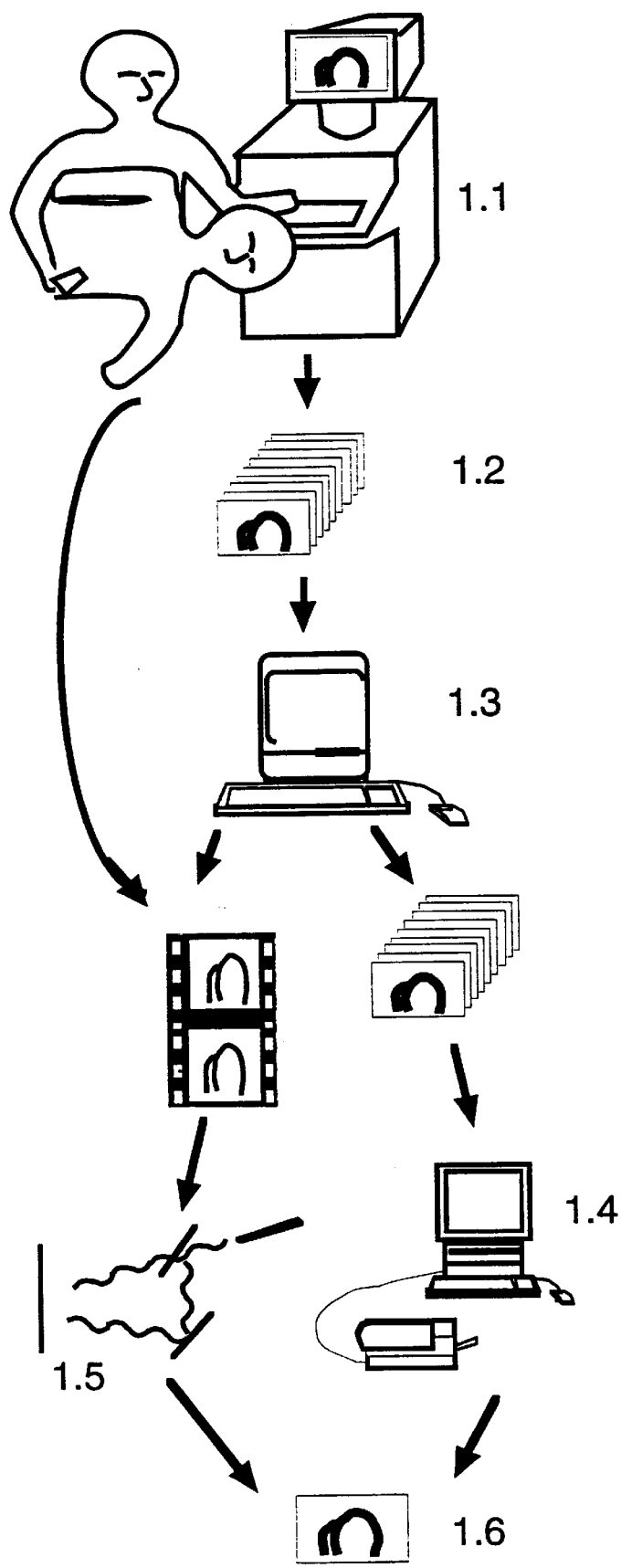
Figure 2:
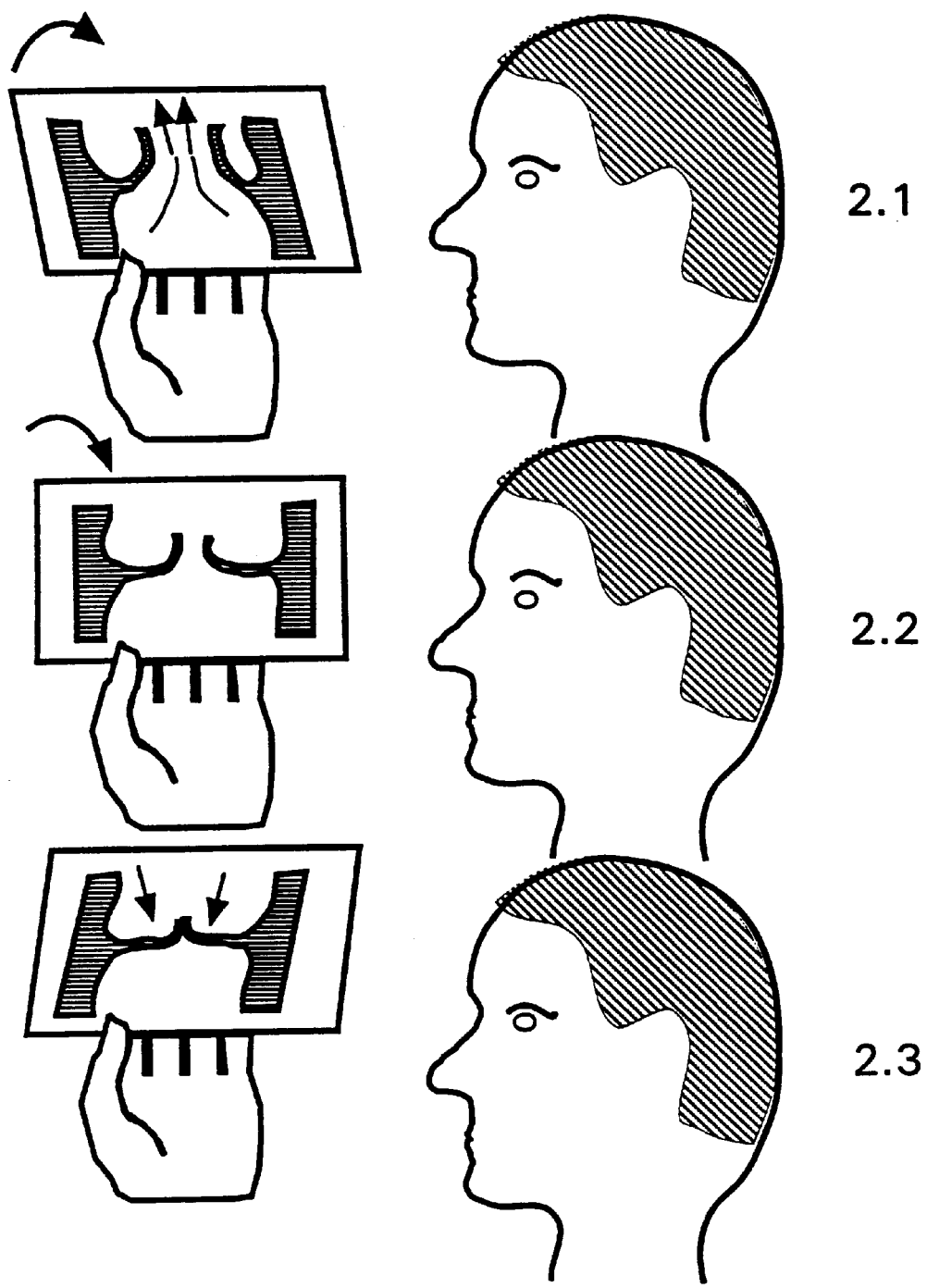

1.1) A dataset is acquired by echocardiography.

1.2) A series of consecutive frames is transferred to an imaging workstation.

1.3) The datasets are reformatted, cropped and filtered.

1.4) The dataset is then transferred to digital holographic printer or alternatively 1.5) conventional optical holography is used to produce the final hologram (1.6).

Drawing 2

Tilting of the resulting hologram (in this case, in vertical direction) leads to the perception of heart motion by the observer:

2.1) The mitral heart valve (left sided inlet valve) is open.

2.2) The mitral valve is closing.

2.3) The mitral valve is closed.

DETAILED DESCRIPTION

According to the invention, a method to display heart motion image data in a portable display medium is provided.

Heart image sequences of human hearts or of experimental animal hearts are acquired by ultrasound (transthoracic or transesophageal echocardiography), computer tomography, magnetic resonance imaging or other biomedical imaging techniques (Drawing 1.1). When using older standard clinical echocardiographic machines, digitization of the analog video signal by a video digitizer was necessary. In contrast, we found it advantageous to use the latest generation echocardiographic machines (e.g., the types Hewlett Packard Sonos 5500, Sonotron Vingmed System 5, Acouson Sequoia) which allows direct storage of the digitally acquired image information, thereby avoiding the image degrading analog step. Thus, digital datasets consisting of a series of 2D frames (or of 3D datasets) are produced (1.2), which represent consecutive timepoints of the heart cycle, and which typically consist of 15–400 frames per beat in 2D motion imaging and of >800 frames per beat in 3D motion imaging. The conventional format for black-and-white images is 8 bit image depth with an image size of around 640*480 pixels image resolution, which was found to offer enough dynamic range for good results. Color images with a higher image depth, e.g. 24 bit, can also be used.

After the dataset is transferred to an imaging workstation (both Compaq PC and a Macintosh PowerPC were used), it is converted to a non-proprietary format, if necessary; this was easiest for the cited Vingmed machine which exports the datasets in a nonproprietary, easily readable format; for Hewlett Packard Sonos 2500, this is achieved by the manufacturer supplied software DSR2TIFF; for Acouson Sequoia, the MountainView Software Package, supplied by the manufacturer, could be used. Then, spatial and/or temporal filtering may be applied (1.3): Best results were achieved by enhancing the image contrast, through the histogram equalization algorithm or manual adjustment, thereby presenting the cavity of the heart as mostly black, the heart valve tissue as maximum brightness, and the heart muscle tissue as intermediary grays.

By assembling several (typically four) loops into the same dataset, side-by-side, it is possible to compare different views of the same heart or similar views of different hearts easily.

These postprocessed datasets are then transferred to a workstation for production of a computational holographic stereogram, or alternatively optical holography can be used to produce a hologram. For hologram production, the sequence information (time) is interpreted as a change in viewing angle in vertical parallax; i.e. subsequent images, each with a time lag dt are dealt with as if dt represents a change in viewing angle alpha. For example, for a dataset of 30 consecutive time-consecutive frames, and a hologram viewing range of 30 degrees, each consecutive frame is assigned an increasing viewing angle in steps of one degree.

From this "pseudo-spatial" dataset, an angularly multiplexed hologram is produced using standard hologram production techniques. Image sequences are incorporated in angularly multiplexed holograms so that the parallax, i.e. the relative position of observer and holographic medium, encodes time. In prior art, many methods are known which allow creation of a hologram using multiple frames. In computational holography (1.4) the fringe pattern is computed, which would be produced by interference of a reference laser beam with a laser beam illuminating an object. By contrast, a hologram is created in optical holography (1.5) by creation of the fringe pattern with actual use of the laser light for object illumination and as reference beam. The photosensitive medium is then exposed to this fringe patterns to create the hologram.

In summary, the perception of heart motion (time progression) in the resulting hologram is achieved by incorporating the time sequence into a spatial parallax, which can then be viewed by tilting the hologram (Drawing 2). Best results are achieved by using the vertical parallax for encoding time, because the two eyes of the observer have a different lateral viewing angle, but the same horizontal viewing angle relative to the hologram. When the horizontal parallax is used for motion display, it tends to confuse the observer, because a different heart phase is seen by each eye. The described invention makes it possible to reduce an image loop of the beating human heart to a single "printable" image which can be used for display, storage, documentation and reporting, e.g. in echocardiography or other medical imaging techniques.

The ability of holography to represent multiple dimensions, conventionally used to convey 3-dimensional space, is therefore expanded to display heart motion. Three-dimensionality can, in addition, be represented by encoding it in the other (usually lateral) parallax using computational holography. Any holographic printing method can be used to print the hologram, if the method can substitute time-consecutive datasets for the customarily used multiple perspective views.

Holograms can be exposed on different media, for example, photopolymer foils (exemplified by the Polariod Mirage holographic film) or silver halide substrates. When the hologram is printed as a reflection hologram (in contrast to a transmission hologram, which offers less impressive results), a simple point-light source is sufficient for optimal viewing of the hologram, making complicated, heavy or expensive viewing devices, like VCR and video screens superfluous.

When the hologram is printed on a portable medium, e.g. on a sheet of photopolymer holographic film, it can be used to review a study outside the medical or holographic imaging laboratory, sent with a exam report, or used for archiving, both in the imaging lab or in a patients chart.

This is particularly useful because other methods to display, report and store heart motion images rely on heavy and expensive equipment which is usually not portable.

By image sequences is meant a series of datasets or images displaying consecutive phases of the heart cycle. Acquisition methods include rapid acquisition of one or of a few heartbeats, or electrocardiogram-triggered acquisition of an entire dynamic dataset over many heart beats. Image sequences can consist of series of digital datasets or of analog (e.g. motion picture) images.

Image sequences include multi-dimensional datasets containing 3-dimensional and time information. To incorporate moving 3-dimensional datasets into a cardiac motion display, the dataset is first split into a time-sequential series of static 3-dimensional datasets. Then, each of these sets is volume rendered or surface rendered, using standard digital imaging techniques. Holograms can be multiplexed in one angular parallax or in two perpendicular parallaxes. For holograms which are multiplexed in only one parallax, one perspective view of each of the mentioned time-sequential static 3D dataset is calculated by using standard digital imaging techniques. The resulting frames are incorporated into an angularly multiplexed hologram as described above. Alternatively, moving 3D datasets can be used to produce holograms which include time in one (usually vertical) parallax and an additional spatial dimension in the other (usually lateral) parallax. To that end, multiple perspective views for each time-sequential static 3D datasets are volume- or surface-rendered. These multiple perspective views are used to multiplex the hologram horizontally. This procedure is repeated with each consecutive static 3D dataset in the vertical parallax. The resulting hologram will show a three-dimensional heart image when held still. When the hologram is rotated laterally, the observer sees the heart rotating around its axis, and when the hologram is tilted vertically, the observer sees heart motion (contraction, valve closure etc).

Likewise, image sequences include representations of heart motion derived from the above mentioned sequences, which were, e.g., postprocessed to enhance or isolate borders.

Image sequences can be monochrome or multicolor, and can include image sequences with color-coded velocity information of cardiac tissue or intracardiac blood, e.g. derived from Doppler techniques. Blood pool color Doppler allows the observer to visualize the temporal pattern of blood flow within the heart in a printable format.

Each individual frame of a sequence may consist of multiple layers, e.g. overlay information from border detection algorithms.

The terms holography or hologram are meant to include all techniques that integrate multiple image dimensions in a flat, solid display medium by means of a fringe pattern. Multiple techniques have been described in prior art to create holograms by exposure of photosensitive substrates to a fringe pattern. They include optical holography which uses object illumination and a reference laser beam to produce the interference pattern. Also included are holographic stereography and other forms of computational holography, that compute the fringe pattern produced if object illumination and reference laser beam were used.

By holographic printer is meant any machine or process which is capable of producing a hologram as defined above.

Another aspect of the invention is the review of heart motion in slow motion, still image or reverse time display, which are easily achieved by tilting the hologram in the desired speed. This is especially useful for detailed study of heart valve motion abnormalities or determination of regional and global heart muscle contractility. A further application of this invention is its use for comparing heart muscle contractility and valve function during consecutive stages of heart stress testing. During this procedure, a patient's heart is subjected to pharmacologic stimulation to produce both increased heart rate and increased contractile velocity, thereby permitting the diagnosis or exclusion of coronary heart disease. While the stress test results are conventionally described verbally, reviewed on videotapes or on a computer in quad-screen format, the present invention is able to print several stages of the stress test side-by-side on a holographic printout, thereby allowing direct comparison of the contractility of the heart muscle in normal speed or slow-motion.

A further practical application of this invention is the representation of moving three-dimensional heart images which may convey more easily understandable and more rapidly readable information than 2-dimensional images of the heart.

Former methods of producing holograms were very time consuming, especially if done by a two step procedure with the intermediate of a "master hologram". As a result, holograms were not widely used in clinical practice. With the development of holographic one step printers allowing production of holograms based on digital datasets within minutes, the current invention is applicable in clinical practice today. Those skilled in the art will be able to ascertain, using no more than routine experimentation, many equivalents of the specific procedures of the invention described herein. These and all other equivalents are intended to be encompassed by the claims made in this invention.

The following non-limiting example further illustrates the present invention.

EXAMPLE

Creation of a hologram representing a so-called four chamber view of the human heart acquired by echocardiography This example illustrates a typical proceeding to create a representation of both heart muscle activity and heart valve closure and opening.

A volunteer underwent an echocardiographic study. Images were acquired using a Hewlett Packard Sonos 2500 echocardiographic machine, using the apical imaging window and a standard four-chamber probe orientation. A standard clinical 2.5 MHz echocardiography transducer was used. Electrocardiographic triggering was used for acquisition timing. Image loops containing 30 images per heartbeat were acquired and digitally stored on a magnetooptical disk.

Image loops consisted of individual frames with a format of 640*480 pixels and an image depth of 8 bits in black and white.

The image loops were then transferred from the disk onto a Compaq Personal Computer and reformatted into a format suitable for postprocessing. Using the NIH image software on a Macintosh PowerPC 7200 computer, image contrast was enhanced and noise was filtered. Image loops were cropped and enlarged to the desired format and resolution.

Images were then transferred to a UNIX workstation. Holographic reflection stereograms were then printed using a one-step holographic stereogram printer, with an image resolution of 640*480 pixels. Using vertical multiplexing, each of the time-sequential frames was incorporated into increasing viewing angle of a hologram which was exposed onto a holographic photopolymer foil.

The resulting hologram displayed the left and the right ventricle, the mitral and the tricuspid valve and the atria. When tilted, the motion of the heart was conveyed: the heart muscle first contracts, then relaxes, and the heart valve closing and opening are clearly seen. The tilting speed can be varied or stopped in any desired position to examine a structure or a motion pattern at the desired phase of the heart cycle. Dimensions on the print accurately reflect dimensions on the original image without visible distortion. Sharpness of the hologram is similar to the sharpness of the original.

What is claimed is:

1. A method for displaying a hologram of heart motion on a portable medium, comprising:

providing an image sequence from the beating heart;

integrating the heart motion sequence into an angularly multiplexed hologram so that one holographic parallax encodes heart motion: and displaying the hologram of the heart on a portable medium.

2. The method of claim 1 further including the step of acquiring the image sequence by one of echocardiography, magnetic resonance imaging, computer tomography, and szintigraphy.

3. The method of claim 1 wherein said image sequence depicts one of the whole heart, heart valves, and intracardiac blood flow.

4. The method of claim 1 wherein said image sequence comprises information derived from imaging one of heart tissue and intracardiac blood.

5. The method of claim 1 wherein said image sequence is a dataset of two or three spatial dimensions, including cross-sectional images, and including volume- and surface-rendered datasets.

6. The method of claim 1 to include one of display, storage and reporting of heart motion.

7. The method of claim 1 wherein said hologram is based on one of interference and diffraction.

8. The method of claim 1 wherein said hologram is based on one of optical holography and computational holography, and holographic stereograms.

9. The method of claim 1 wherein said hologram is one of a transmission hologram and a reflection hologram.

* * * * *